United States Patent [19]

Graiver et al.

[11] Patent Number: 5,708,115
[45] Date of Patent: Jan. 13, 1998

[54] POLYMERIZATION OF VINYL MONOMERS FROM SILANES AND SILOXANES

[75] Inventors: Daniel Graiver, Midland, Mich.; Aaron Quoc Khieu, Coon Rapids, Minn.; Binh Thanh Nguyen, Midland, Mich.

[73] Assignee: Dow Corning Corporation, Midland, Mich.

[21] Appl. No.: 798,990

[22] Filed: Feb. 11, 1997

[51] Int. Cl.$^6$ .................................. C08G 77/14
[52] U.S. Cl. .................... 528/32; 549/214; 528/37; 528/40; 528/38
[58] Field of Search ............... 549/214; 528/37, 528/40, 32, 38

[56] References Cited

U.S. PATENT DOCUMENTS

| | | | |
|---|---|---|---|
| 3,509,191 | 4/1970 | Atwell | 260/448 |
| 4,599,439 | 7/1986 | Misra | 556/443 |
| 4,609,574 | 9/1986 | Keryk | 427/407 |
| 4,658,044 | 4/1987 | Ravenscroft | 549/415 |
| 4,677,211 | 6/1987 | Jewell, Jr. et al. | 548/491 |

OTHER PUBLICATIONS

Macromol. Chem. Phys., vol. 195, pp. 1673–1685, 1994.
Doklady Physical Chemistry, vol. 268, Nos. 1–3, pp. 156–160, 1983.
Ozone Chemistry & Technology, Franklin Press, pp. 257–278, 1975.
Cem. Review, vol. 36, 284+, 1967.
Otkrytiia Izobreteniia Promyshlennye Obraztsi Tovarnye Znaki 54 (48) pp. 89 (1977).
Journal of Polymer Science, Part A, Polymer Chemistry, vol. 31, pp. 1035–1043, 1993.
Journal of Polymer Science, Part A, Polymer Chemistry, vol. 32, pp. 1377–1384, 1994.
Journal Organic Chemistry, vol. 39 (11), pp. 1539–1542, (1974).

*Primary Examiner*—Margaret W. Glass
*Attorney, Agent, or Firm*—James L. Decesare

[57] ABSTRACT

A method in which radical polymerization of a vinyl monomer is initiated by an ozonide group attached to a silane or a siloxane polymer. The method is particularly useful for preparing organic polymers having a silicone chain end, or for preparing wide ranges of silicone/organic polymers and copolymers with varied architecture, i.e., ABA block copolymers, comb polymers, star polymers, and hyperbranched polymers. In one embodiment, the method is carried out by simply heating a vinyl monomer in the presence of a silane containing ozonide functionality. The ozonide silane is obtained by exposing silanes or siloxanes having an alkyl group containing a double bond to ozone. Surprisingly, an ozonide attached to an organosilicon compound was found to be stable, and capable of initiating vinyl polymerization upon heating to moderate temperatures, i.e., about 70° C.

6 Claims, No Drawings

POLYMERIZATION OF VINYL MONOMERS FROM SILANES AND SILOXANES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention is directed to initiation of radical polymerization of organic monomers, and more particularly to the use of ozonide functional silanes and ozonide functional siloxanes as free radical initiators.

The free radical initiation of polymerization of vinyl monomers with peroxides and other highly oxygenated compounds is known. Polymerization can be initiated when such unstable peroxides and oxygenated compounds decompose to form free radicals, which then react, with the vinyl monomer resulting in polymerization of the vinyl monomer. However, the use of these free radical initiators has been limited to only relatively stable initiators. As a consequence, it has been proposed to use ozone $O_3$ to initiate the graft polymerization of one polymer to the surface of another polymer, primarily, to change the properties associated with the surface of the other polymer. In many cases, however, this reaction of $O_3$ with the polymer surface, and the structure of the oxidative surface, is not well defined, and depends to a large extent on the chemical structure of the polymer.

For example, when olefins (alkenes) are used, the cleavage of C=H bonds and formation of free radicals has been observed during ozonolysis of isotactic polypropylene, whereby polymers containing unsaturation undergo rearrangement or rupture of the unsaturated bonds. In either case, intermediates are formed, typically having short lifetimes, and therefore the intermediates must be used promptly in polymerizing vinyl monomers.

It is therefore desirable to take advantage of the simplicity of the ozonolysis reaction, but to produce instead stable, well-defined ozonide intermediates, that can be used at will to initiate vinyl polymerization.

One such example has been obtained by treating the compound bicyclo[2.2.1]hept-2-ene which is shown below

Norbornylene(bicyclo[2.2.1]hept-2-ene, norbornene)

with ozone, i.e., Otkrytiia Izobreteniia Promyshlennye Obraztsi Tovarnye Znaki 54 (48) Page 89, (1977).

However, it would be further desirable to have a stable ozonide attached to an organosilicon compound, i.e., a silane or a siloxane polymer, such that by using an organosilicon ozonide to initiate vinyl polymerization, a polymer having organosilicon end-groups would be obtained.

BRIEF SUMMARY OF THE INVENTION

Our invention relates to a composition which is an organosilicon compound containing ozonide functionality; and to the method of making an organosilicon compound containing ozonide functionality, by exposing an organosilicon compound containing olefinic unsaturation to ozone.

Our invention is also related to a polymerization method in which the polymerization of a polymerizable organic monomer is initiated by heating the polymerizable organic monomer in the presence of an organosilicon compound containing ozonide functionality; and to the polymers or copolymers prepared according to this method.

One type of organosilicon compound containing ozonide functionality which is used can be represented by the structure

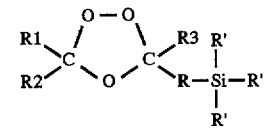

or

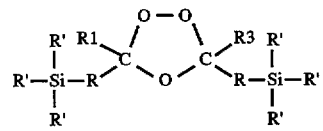

in which R is the residue of an unsaturated radical bound to silicon; R1, R2, and R3, are hydrogen, an alkyl radical, or an aryl radical; and R' is an alkyl radical, an aryl radical, a hydrolyzable group, an organosiloxy radical, or a polyorganosiloxy radical.

The organo substituents of the organosiloxy and polyorganosiloxy radicals may be any of the organo substituents suitable for bonding to silicon atoms. Typical organo substituents for these radicals include hydrocarbon radicals such as alkyl radicals and aryl radicals.

Another type of organosilicon compound containing ozonide functionality which can be used is an ozonide bound cycloalkyl silane in which the silicon atom is part of a ring structure, or an ozonide bound cycloalkyl silane in which the silicon atom is not part of a ring structure.

These and other features of our invention will become apparent from a consideration of the detailed description.

BRIEF DESCRIPTION OF THE SEVERAL VIEWS OF THE DRAWING

Not applicable.

DETAILED DESCRIPTION OF THE INVENTION

According to our invention, we provide a well-defined and relatively stable compound having an ozonide group attached to an organosilicon molecule. Upon heating the compound in the presence of a vinyl monomer, the compound decomposes and initiates polymerization. As a result, the organosilicon portion of the initiator becomes an integral part of the resulting organic polymer.

The ozonolysis of certain alkenes leads to the formation of an ozonide intermediate. The ozonide intermediate is a five-member peroxy-ether ring shown in the formula:

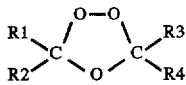

in which R1, R2, R3, and R4, are hydrogen, an alkyl group such as methyl, or an aryl group such as phenyl. When R1, R2, R3, and R4, are each hydrogen, for example, the ozonide is 1,2,4-trioxolane. When R1 and R3 are hydrogen, and R2 and R4 are methyl, for example, the ozonide is 3,5-dimethyl-1,2,4-trioxolane.

These ozonide intermediates are not stable, and readily rearrange to various hydroperoxides, dimeric and polymeric peroxides, and other oxygen containing compounds. According to the literature, it is generally agreed that in most cases, these ozonides break down rapidly, and initially form more stable zwitterion intermediates.

However, we have surprisingly observed that organosilicon compounds containing ozonide groups remain stable, even in the presence of zinc and acetic acid, which are known to reduce organic ozonide intermediates to stable carbonyl compounds. Decomposition of our ozonide compounds in the presence of zinc and acetic acid is complete only when the reaction mixture is heated to 32° C. for one hour.

Therefore, since our ozonide bound organosilicon compounds are relatively stable at room temperature (20°–25° C./68°–77° F.), and decompose only at elevated temperature, they can be used to initiate vinyl monomer polymerization. For example, where an ozonide is attached to a silane, an organic polymer terminated by a silane group is obtained.

Functional silanes having hydrolyzable substituents such as halosilanes, alkoxysilanes, and acetoxysilanes can be used, in which case, after the initial vinyl monomer polymerization, subsequent polycondensation of these terminal silanes with other siloxane monomers or oligomers yields block copolymers. The structure of the block copolymer will depend upon the structure of the functional silane. For example, A/B-type block copolymers (i.e., AAAABBBBB where A is the organic block and B is the silicone block) are obtained when silanes having one alkenyl group and one hydrolyzable group, as described above, are attached to the silicon atom. ABA-type block copolymers (i.e., AAAABBBBBAAAA where A is the organic block and B is the silicone block) are obtained when silanes having two alkenyl groups and one hydrolyzable group, as described above, are attached to the silicon atom. More complicated block copolymer structures are possible with silanes having larger numbers of groups that can be polymerized by either polycondensation or radical polymerization.

Some examples of functional silanes, and silanes most preferred according to our invention, are silanes in which the unsaturation is at least two carbon atoms removed from the silicon atom, such as butenylmethyldichlorosilane, 5-hexenyldimethylchlorosilane, 5-hexenylmethyldichlorosilane, 5-hexenyltrichlorosilane, 7-octenyldimethylchlorosilane, 7-octenyltrichlorosilane, 1,10-bis(dimethylchlorosilyl)-5-decene, 3-butenyltriethoxysilane, 5-hexenyldimethylmethoxysilane, 5-hexenylmethyldimethoxysilane, and 7-octenyltrimethoxysilane.

While functional silanes having hydrolyzable substituents such as halosilanes, alkoxysilanes, and acetoxysilanes, are most preferred herein, functional silanes having other types of hydrolyzable substituents can be used, such as amino, ketoxime, ureido, carboxyl, sulfate, sulfate ester, cyano, isocyanate, phosphate, and phosphate ester.

If the ozonide is bound to an organosiloxane polymer, grafting of the organic monomer onto the silicone polymer is obtained. The structure of such graft copolymers will depend upon the position of the ozonide along the organosiloxane polymer chain. Thus, a telechelic ozonide will lead to an ABA block structure, and a pendant ozonide will lead to a polymer comb. As used herein, the term "telechelic" is intended to mean a polymer that contains end groups that react selectively to give a bond with another molecule.

Most preferred for use herein are polysiloxanes containing telechelic alkenyl groups. Suitable alkenyl functional siloxanes and methods for their preparation are described, for example, in U.S. Pat. No. 4,609,574 (Sep. 2, 1986), incorporated herein by reference.

In general, these materials can be described as being made up of diorganosiloxane "D" units $R_2^a SiO_{2/2}$ and chain terminating "M" units $R_3^a SiO_{1/2}$ where $R^a$ is a methyl radical or a hydrocarbon radical containing unsaturation. The unsaturated radicals include higher alkenyl radicals such as $-(CH_2)_m-CH=CH(CH_2)_n H$, where m has a value of 2, 3, or 4; and n has a value of 0, 1, or 2; although m can exceed 4, and n can exceed 2, if desired. The unsaturation need not be in the terminal position of the hydrocarbon. However, it must be at least two carbon atoms removed from the silicon atom.

Other types of organosilicon compounds containing unsaturation can be used, in addition to the functional silanes and alkenyl functional siloxanes referred to above. For example, cycloalkyl silanes can be used, including cycloalkyl silanes in which the silicon atom constitutes part of the ring structure. Such cycloalkyl silanes are represented below:

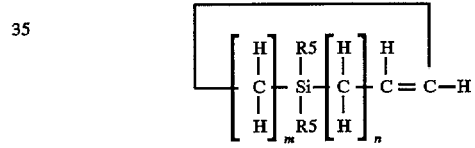

Compounds illustrative of this type of cycloalkyl silane are described, for example, in the *Journal of Organic Chemistry*, Volume 39 (11), Pages 1539–1542, (1974). In this type of cycloalkyl silane, m and n each have a value of 2–4, and R5 can be an alkyl radical, an aryl radical, or one of the hydrolyzable groups previously described. As noted above, the unsaturation should be at least two carbon atoms removed from the silicon atom.

In addition, cycloalkyl silanes can be used of the type in which the silicon atom does not constitute part of the ring structure. Such cycloalkyl silanes are represented below:

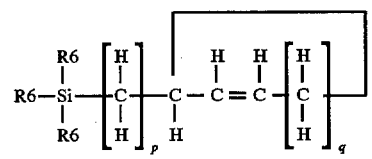

In this type of cycloalkyl silane, p is 1–4; q is 2–6; and R6 represents an alkyl radical, an aryl radical, or one of the hydrolyzable groups previously described. The unsaturation should be at least two carbon atoms removed from the silicon atom.

An alternate embodiment of the cycloalkyl silane shown immediately above is represented below:

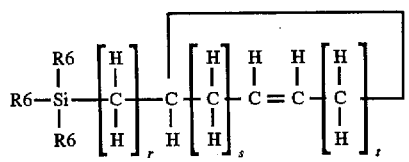

In this alternate embodiment of cycloalkyl silane, r is 0–4; s and t are each 1–6; and R6 represents an alkyl radical, an aryl radical, or one of the hydrolyzable groups previously described. The unsaturation should be at least two carbon atoms removed from the silicon atom.

Another type of cycloalkyl silane which can be used of the type in which the silicon atom does not constitute part of the ring structure is represented below:

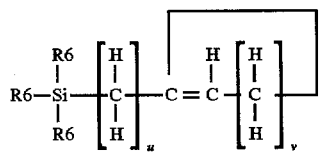

In this type of cycloalkyl silane, u is 2–4; v is 3–7; and R6 represents an alkyl radical, an aryl radical, or one of the hydrolyzable groups previously described. The unsaturation should be at least two carbon atoms removed from the silicon atom.

Some examples of functional cycloalkyl silanes of the type in which the silicon atom does not constitute part of the ring structure are [2-(3-cyclohexenyl)ethyl] dimethylchlorosilane, [2-(3-cyclohexenyl)ethyl] methyldichlorosilane, 3-cyclohexenyltrichlorosilane, [2-(3-cyclohexenyl)ethyl]triethoxysilane, and [2-(3-cyclohexenyl)ethyl]trimethoxysilane.

Our invention can be illustrated schematically in the reaction sequences shown below. For example, ozone attaches itself at a double bond to form an ozonide as follows:

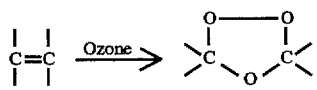

If the double bond is within an organosilane compound, an ozonide bound silane is obtained as follows:

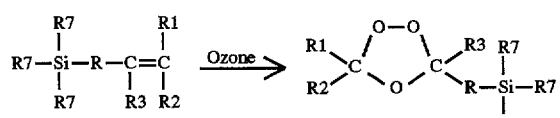

The same results are obtained using an organosilane compound of the following type:

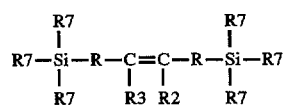

If the double bond is within a polyorganosiloxane molecule, an ozonide bound polyorganosiloxane is obtained as follows:

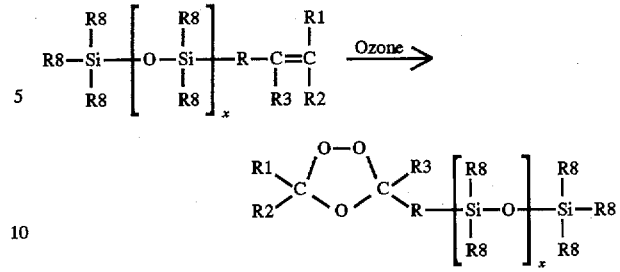

In the following reaction sequence, an ozonide bound cycloalkyl silane in which the silicon atom is part of the ring structure is obtained as follows:

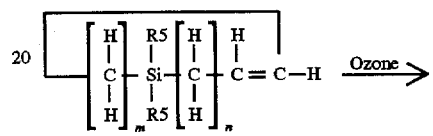

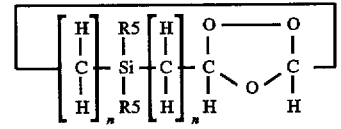

In the following reaction sequence, an ozonide bound cycloalkyl silane in which the silicon atom is not part of the ring structure is obtained as follows:

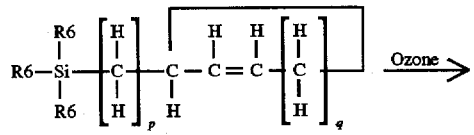

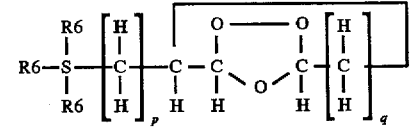

In the following reaction sequence, an alternate embodiment of ozonide bound cycloalkyl silane in which the silicon atom is not part of the ring structure is obtained as follows:

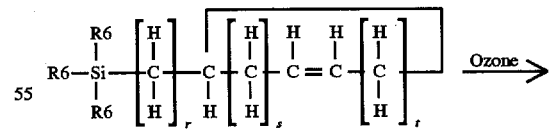

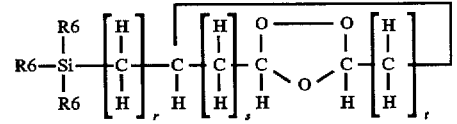

In the following reaction sequence, another type of ozonide bound cycloalkyl silane in which the silicon atom is not part of the ring structure is obtained as follows:

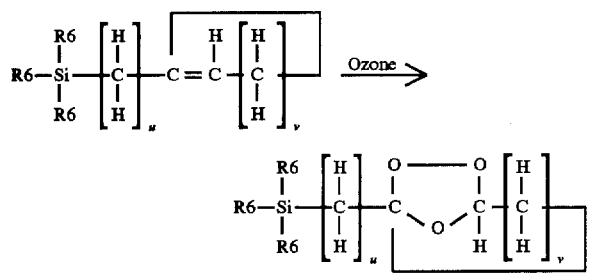

In the following reaction sequence, the ozonide bound silanes or the ozonide bound polysiloxane shown above are represented as "Ozonide", and are used in this reaction sequence in the preparation of a "Polymer Product".

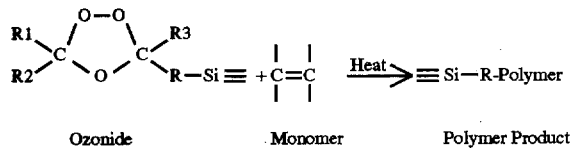

An "Ozonide" bound silane, i.e.,

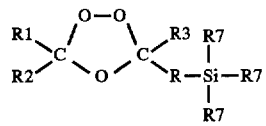

can be prepared according to our Example 1.

An "Ozonide" bound polysiloxane, i.e.,

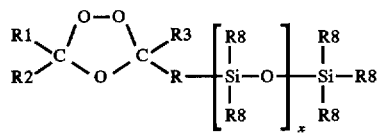

can be prepared according to our Example 2.

It is also possible, according to our invention, to employ in the above reaction sequence, an "Ozonide" of the following type:

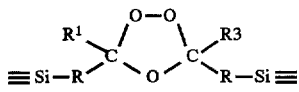

An "Ozonide" bound silane of this type can be represented as:

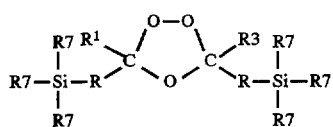

An "Ozonide" bound silane of this type can be prepared according to our Example 3.

An "Ozonide" bound polysiloxane of this type can be represented as:

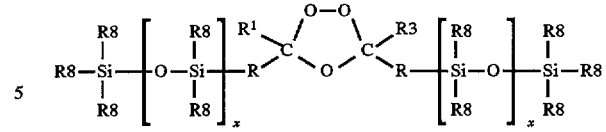

In these "Ozonide" formulas, x has a value of one or more, and R represents the residue of the unsaturation, i.e., for example, when the unsaturation is 5-hexenyl, R would be —$(CH_2)_4$—. Preferably, R should contain at least two carbon atoms. R7 is an alkyl radical, an aryl radical, or one of the functional groups as previously described. R8 is an organic radical, preferably a hydrocarbon radical such as an alkyl group.

The following examples are set forth for the purpose of illustrating our invention in more detail.

EXAMPLE 1

Preparation of an Ozonide Bound Silane 5-hexenyldimethylchlorosilane $H_2C=CH(CH_2)_4$—Si$(CH_3)_2Cl$ was dissolved in D4, the cyclic tetramer octamethylcyclotetrasiloxane (17.43 grams in 150 ml), in a three-neck flask equipped with a stirrer. The solution was cooled to 0° C. Ozone was introduced into bottom of the solution, and was allowed to bubble through the solution at a rate of 0.0213 lb/per hour (0.0268×$10^{-4}$ kilograms per second kg/s). The ozonolysis reaction was completed after 95 minutes as indicated from an intense blue color. Structure was confirmed by $^{13}C$ NMR and gas chromatograph. Thus, the peaks related to the double bond carbons (−114 and −140 ppm) disappeared upon ozonolysis, and the ozonide characteristic peaks assigned to the carbons bonded to the oxygens (−94 and −104 ppm) were observed. No other changes were observed in the NMR spectra.

EXAMPLE 2

Preparation of an Ozonide Bound Polysiloxane

A polysiloxane containing telechelic hexenyl groups was used in this example. The siloxane was a dimethyl 5-hexenylsiloxy-terminated dimethylpolysiloxane with a viscosity of about 170 centistokes (mm²/s) at 25° C. The telechelic siloxane was dissolved in methylene chloride $CH_2Cl_2$ (50 grams in 150 ml) in a three-neck flask equipped with a stirrer. The solution was cooled to −15° C. Ozone was introduced into the bottom of the solution, and allowed to bubble through the solution at a rate of 0.0213 lb/per hour (0.0268×10⁻4 kilograms per second kg/s). $^{13}C$ NMR showed complete conversion to the ozonide intermediate indicated by the presence of no residual double bonds.

EXAMPLE 3

Preparation of Another Ozonide Bound Silane 1,10-bis(dimethylchlorosilyl)-5-decene which is shown below

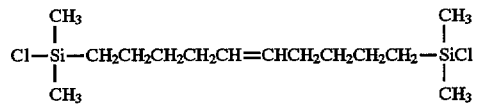

was dissolved in methylene chloride (23.23 grams in 150 ml) in a three-neck flask equipped with a stirrer. The solution was cooled to 0° C. Ozone was introduced into the bottom of the solution, and allowed to bubble through the solution a rate of 0.0213 lb/per hour (0.0268×10⁻⁴ kilograms per second kg/s). The ozonolysis reaction was completed after 80 minutes as indicated by an intense blue color.

EXAMPLE 4

Ozonide Initiated Polymerization of Ethyl Acrylate

A polyethylacrylate having silicone end groups was prepared by polymerizing ethyl acrylate monomer $H_2C=CHCOOC_2H_5$ with the ozonide silane prepared in Example 1. In this example, 15.63 grams of the ozonide-bound silane of Example 1 and 1.03 grams of ethyl acrylate, free of polymerization inhibitors, were mixed and placed in a one ounce bottle. After flushing with nitrogen, the bottle was placed in a constant temperature bath at 70° C. After 60 minutes, the reaction mixture changed from clear to cloudy, and the polymer was precipitated from methanol.

EXAMPLE 5

Ozonide Initiated Polymerization of Ethyl Acrylate

A polyethylacrylate grafted onto the ends of a polysiloxane, i.e., an ABA block copolymer, was prepared by mixing 15.22 grams of the ozonide bound polysiloxane prepared in Example 2 with 8.61 grams of ethyl acrylate monomer, free of polymerization inhibitors, in a one ounce bottle. After flushing with nitrogen to remove oxygen, the bottle was placed in a constant temperature bath set at 70° C. Soon after the clear reaction mixture was placed in the constant temperature bath, it turned cloudy. However, the reaction was allowed to proceed for one hour, and the copolymer was precipitated from methanol.

EXAMPLE 6

Ozonide Initiated Polymerization of Aacrylamide

A polyacrylamide having silicone end groups was prepared by polymerizing acrylamide monomer $H_2C=CHCONH_2$ with the ozonide silane prepared in Example 3. In this example, 21.93 grams of the ozonide bound silane of Example 3 and 3.12 grams of acrylamide, free of polymerization inhibitors, were mixed and place in a one ounce bottle. After flushing with nitrogen to remove oxygen, the bottle was placed in a constant temperature bath at 70° C. After 60 minutes, the reaction mixture changed color from yellow to brown, and the polymer was precipitated in water.

EXAMPLE 7

Comparative Example—No Ozonide Silane

Ethyl acrylate (1.25 grams), free of polymerization inhibitors, was dissolved in 13.24 grams of octamethylcyclotetrasiloxane and placed in a one ounce bottle. After oxygen was removed and replaced with nitrogen, the reaction mixture was placed in a constant temperature bath for one hour as described in Example 4. No change was observed throughout this time and the solution remained clear. No polymer precipitated in methanol. This example indicates that without an ozonide bound group, no polymerization can be obtained.

EXAMPLE 8

Comparative Example—No Silicone

This example shows that a silicone matrix greatly affects the stability of ozonide bound groups. In this example, an ozonolysis reaction was conducted with 1-hexene $CH_3CH_2CH_2CH_2CH=CH_2$ (8.5 grams) in methylene chloride (100 ml) at −78° C. for 30 minutes. The reaction was complete in 40 minutes as indicated by the appearance of a blue color. However, this ozonide was very unstable. Thus, it rapidly decomposed in an uncontrolled exothermic reaction, and splashed out of the reaction flask, shortly after it was brought to room temperature or when the solvent $CH_2C_2$ was removed.

It is our belief that the presence of the siloxane molecule greatly moderates the rate of the decomposition reaction, and reduces the risk of explosion which is likely when dealing with such highly-oxygenated unstable ozonide intermediates. The above examples are summarized below.

TABLE 1

Summary of Examples

| Ex. | Reactant 1 | Reactant 2 | Temp (°C.) | Time (min.) |
|-----|------------|------------|------------|-------------|
| 1 | 5-Hexenyldimethyl chlorosilane | D4 | 0 | 95 |
| 2 | Telechelic Siloxane | $CH_2Cl_2$ | −15 | 10 |
| 3 | 1,10-bis (dimethyl chloro silyl)-5-decene | $CH_2Cl_2$ | 0 | 80 |
| 4 | Chlorosilane ozonide in D4 | Ethyl acrylate | 70 | 60 |
| 5 | Siloxane ozonide in $CH_2Cl_2$ | Ethyl acrylate | 70 | 60 |
| 6 | Dichlorosilane ozonide in $CH_2Cl_2$ | Acrylamide | 70 | 60 |
| 7 | D4 (No ozonide) | Ethyl acrylate | 70 | 60 |
| 8 | 1-Hexene (No silicone) | $CH_2Cl_2$ | −78 | 40 |

Other variations may be made in compounds, compositions, and methods described herein without departing from the essential features of our invention. The forms of our invention are exemplary only and not intended as limitations on its scope as defined in the appended claims.

We claim:

1. A composition comprising an organosilicon compound containing ozonide functionality represented by the structure $$\begin{array}{c} R1 \\ \diagdown \\ R2 \end{array} \!\! C \!\! \begin{array}{c} O-O \\ \diagup \quad \diagdown \\ \diagdown \quad \diagup \\ O \end{array} \!\! C \!\! \begin{array}{c} R3 \\ \diagdown \\ R \end{array} \!\!-\!\! \underset{\underset{R'}{|}}{\overset{\overset{R'}{|}}{Si}} \!\!-\!\! R'$$

or $$R'\!-\!\underset{\underset{R'}{|}}{\overset{\overset{R'}{|}}{Si}}\!-\!R \!\! \begin{array}{c} R1 \\ \diagdown \\ \end{array} \!\! C \!\! \begin{array}{c} O-O \\ \diagup \quad \diagdown \\ \diagdown \quad \diagup \\ O \end{array} \!\! C \!\! \begin{array}{c} R3 \\ \diagdown \\ \end{array} \!\!-\!\! R \!\!-\!\! \underset{\underset{R'}{|}}{\overset{\overset{R'}{|}}{Si}} \!\!-\!\! R'$$

in which R is the residue of an unsaturated hydrocarbon radical containing at least two carbon atoms bound to silicon; R1, R2, and R3, are hydrogen, an alkyl radical, or an aryl radical; and R' is an alkyl radical, an aryl radical, a hydrolyzable group, an organosiloxy radical, or a polyorganosiloxy radical.

2. A composition according to claim 1 in which the organosilicon compound containing ozonide functionality is selected from the group consisting of

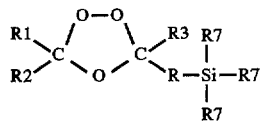

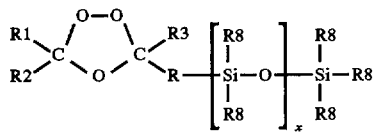

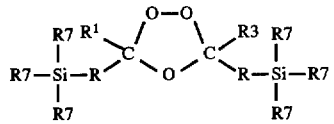

and

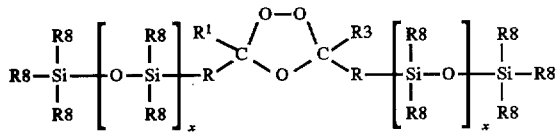

in which x has a value of at least one; R7 is an alkyl group, an aryl group, halogen, alkoxy, or acetoxy; and R8 is a hydrocarbon radical.

3. An organosilicon compound containing ozonide functionality prepared by a method comprising exposing to ozone an organosilicon compound selected from the group consisting of

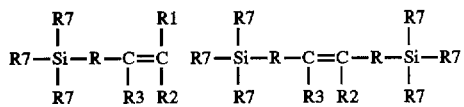

and

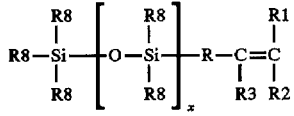

in which R is a hydrocarbon linking group containing at least two carbon atoms; R1, R2, and R3, are hydrogen, an alkyl radical, or an aryl radical; x has a value of at least one; R7 is an alkyl group, an aryl group, halogen, alkoxy, or acetoxy; and R8 is a hydrocarbon radical.

4. A compound according to claim 3 in which the organosilicon compound exposed to ozone is selected from the group consisting of 5-hexenyldimethylchlorosilane, 1,10-bis (dimethylchlorosilyl)-5-decene, and a dimethylhexenylsiloxy-terminated dimethylpolysiloxane.

5. An organosilicon compound containing ozonide functionality prepared by a method comprising exposing to ozone an organosilicon compound selected from the group consisting of

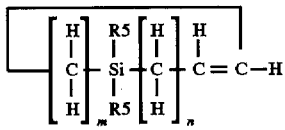

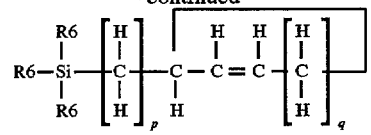

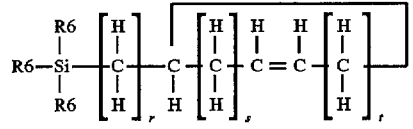

and

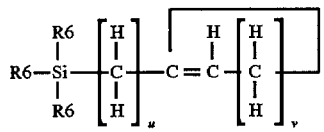

wherein m and n each have a value of 2–4; p is 1–4; q is 2–6; r is 0–4; s and t are each 1–6; u is 2–4; v is 3–7; and R5 and R6 represent alkyl, aryl, halogen, alkoxy, or acetoxy.

6. A composition comprising an organosilicon compound containing ozonide functionality in which the organosilicon compound is a cycloalkyl silane selected from the group consisting of cycloalkyl silanes in which the silicon atom is part of a ring structure, and cycloalkyl silanes in which the silicon atom is not part of a ring structure but in which there are at least two carbon atoms between the silicon atom and the ozonide functionality, the organosilicon compound containing ozonide functionality being selected from the group consisting of

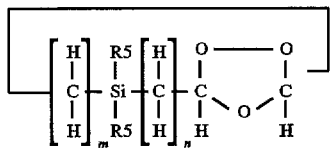

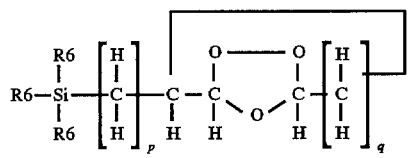

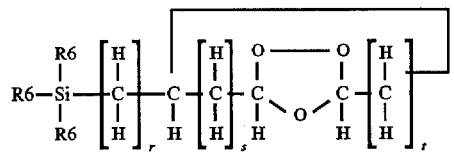

and

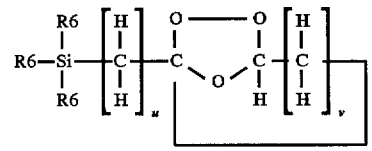

wherein m and n each have a value of 2–4; p is 1–4; q is 2–6; r is 0–4; s and t are each 1–6; u is 2–4; v is 3–7; and R5 and R6 represent alkyl, aryl, halogen, alkoxy, or acetoxy.

* * * * *